(12) United States Patent
Küçük (10) Patent No.: US 11,932,449 B2
(45) Date of Patent: Mar. 19, 2024

(54) HOLDING DEVICE WHICH RESTRICTS MOVEMENT OF PRIMARY PACKAGING CONTAINERS AT FIRST AND FURTHER LONGITUDINAL POSITIONS WITH A DISTANCE

(71) Applicant: SCHOTT Pharma Schweiz AG, St. Gallen (CH)

(72) Inventor: Mustafa Küçük, Staad (CH)

(73) Assignee: SCHOTT Pharma Schweiz AG, St. Gallen (CH)

( * ) Notice: Subject to any disclaimer, the term of this patent is extended or adjusted under 35 U.S.C. 154(b) by 0 days.

(21) Appl. No.: 17/483,321

(22) Filed: Sep. 23, 2021

(65) Prior Publication Data
US 2022/0097914 A1    Mar. 31, 2022

(30) Foreign Application Priority Data
Sep. 25, 2020  (EP) .................................... 20198372

(51) Int. Cl.
| | |
|---|---|
| *A61J 1/16* | (2023.01) |
| *A61M 5/00* | (2006.01) |
| *B65D 25/10* | (2006.01) |
| *B65D 77/20* | (2006.01) |

(52) U.S. Cl.
CPC ........... *B65D 25/108* (2013.01); *A61M 5/002* (2013.01); *B65D 77/2024* (2013.01)

(58) Field of Classification Search
CPC ...... A61M 5/001; A61M 5/002; A61M 5/008; A61J 1/16; B65D 77/2024; B65D 25/108

USPC .................................................. 206/364, 438
See application file for complete search history.

(56) References Cited

U.S. PATENT DOCUMENTS

| | | | | |
|---|---|---|---|---|
| 8,460,622 | B2 * | 6/2013 | Motadel ................ | B01L 3/0275 |
| | | | | 422/526 |
| 8,505,723 | B2 * | 8/2013 | Clark ..................... | B65D 5/503 |
| | | | | 206/443 |
| 9,555,911 | B2 * | 1/2017 | Pawlowski ........... | A61M 5/001 |
| 9,718,583 | B2 * | 8/2017 | Nicoletti ................ | B65D 65/02 |
| 9,776,188 | B1 * | 10/2017 | Kamees .................... | B01L 9/50 |

(Continued)

FOREIGN PATENT DOCUMENTS

| | | |
|---|---|---|
| WO | 2014/049713 A1 | 4/2014 |
| WO | 2019/030782 A1 | 2/2019 |

*Primary Examiner* — Steven A. Reynolds
(74) *Attorney, Agent, or Firm* — Taylor IP, P.C.

(57) ABSTRACT

An arrangement includes a holding device for holding primary packaging containers. The holding device includes: a secondary packaging container which is designed and arranged for accommodating the primary packaging containers; holding elements of a first kind arranged in the secondary packaging container, each holding element of the first kind is designed and arranged to detachably hold a primary packaging container by contacting the primary packaging container at a first longitudinal position of the primary packaging container; and holding elements of a further kind arranged in the secondary packaging container. For each holding element of the first kind, a holding element of the further kind is designed and arranged to restrict a movement of the primary packaging container, which is held by the holding element of the first kind, in a lateral direction of the primary packaging container at a further longitudinal position of the primary packaging container.

18 Claims, 7 Drawing Sheets

(56) References Cited

U.S. PATENT DOCUMENTS

| | | | |
|---|---|---|---|
| 11,161,671 B2* | 11/2021 | Yoshida | A61M 5/008 |
| 2005/0236346 A1 | 10/2005 | Whitney | |
| 2007/0286775 A1 | 12/2007 | Yong | |
| 2009/0100802 A1 | 4/2009 | Bush et al. | |
| 2012/0328489 A1* | 12/2012 | Beese | B65D 25/108 |
| | | | 422/526 |
| 2013/0186793 A1* | 7/2013 | Gagnieux | A61M 5/002 |
| | | | 206/364 |
| 2015/0108034 A1* | 4/2015 | Deutschle | B01L 9/06 |
| | | | 206/593 |
| 2016/0108020 A1* | 4/2016 | Kennis | A61P 9/10 |
| | | | 514/266.22 |
| 2018/0208377 A1* | 7/2018 | Kloke | A61J 7/0069 |

* cited by examiner

HOLDING DEVICE WHICH RESTRICTS MOVEMENT OF PRIMARY PACKAGING CONTAINERS AT FIRST AND FURTHER LONGITUDINAL POSITIONS WITH A DISTANCE

CROSS REFERENCE TO RELATED APPLICATIONS

This application claims priority to European Patent Application No. EP 20198372.3, filed on Sep. 25, 2020, which is incorporated in its entirety herein by reference.

BACKGROUND OF THE INVENTION

1. Field of the Invention

The present invention relates to a holding device for holding a plurality of primary packaging containers for pharmaceutical, medical or cosmetic compositions, the holding device comprising a secondary packaging container which is designed and arranged for accommodating the plurality of primary packaging containers. Further, the invention relates to an arrangement including the holding device, and to a use of the arrangement for storage, transport or filling of the primary packaging containers.

2. Description of the Related Art

Containers made from glass and later on also from polymer have been applied for transporting fluids and powders safely for a long time. In the last decades, the arts in which glass and polymer containers are used for transporting fluids and powders have become increasingly diverse and sophisticated. One such art is the technical field of the present application: pharmaceutical packaging. In the pharmaceutical industry, containers—such as vials, syringes, ampoules and cartridges—are applied as primary packaging for all kinds of pharmaceutically relevant compositions, in particular drugs, such as vaccines, and also for cosmetic compositions, in particular cosmetic compositions which are to be injected into the skin.

In the processing of containers for use in pharmaceutical or cosmetic applications, generally so-called nested solutions are preferred nowadays, where a plate-like holding structure for containers (also referred to as nest) is used for concurrently holding or supporting a plurality of containers in a given configuration. The nests are usually delivered to a customer, such as a pharmaceutical company or filler, packaged in a transport or packaging container (also referred to as tub). For further processing the containers, the tubs are opened. Further processing the containers often includes automated steps of removing the containers from the tub; filling the containers with a composition, e.g. a pharmaceutical or cosmetic composition; closing the pre-filled containers, e.g. in case of syringes by applying a hypodermic needle via a Luer taper; and vacuum packaging individual containers in thin foil bags for retail. Aspects of patient safety and suitability of the nest for automated processing may suffer from harsh conditions during transport and also from storage of the nest filled with containers.

What is needed in the art is a way to at least partly overcome a disadvantage arising from the prior art. What is also needed in the art is a nest which, in terms of patient safety, is more suitable to accommodate primary packaging containers for pharmaceutical, medical or cosmetic compositions, such as syringes, vials, cartridge and ampoules, during transport. Here, patient safety, in particular, refers to a Container Closure Integrity (CCI) of the primary packaging containers after transport or to a particle load of the primary packaging containers after transport or both. What is also needed in the art is a nest for packing primary packaging containers for pharmaceutical, medical or cosmetic compositions, such as syringes, vials, cartridges and ampoules, where the nest is more suitable for being further processed by an auto-mated filling machine.

SUMMARY OF THE INVENTION

In some exemplary embodiments provided according to the invention, an arrangement includes a holding device for holding a plurality of primary packaging containers for pharmaceutical, medical or cosmetic compositions. The holding device includes: a secondary packaging container which is designed and arranged for accommodating the plurality of primary packaging containers; a plurality of holding elements of a first kind arranged in the secondary packaging container, each holding element of the first kind is designed and arranged to detachably hold a primary packaging container of the plurality of primary packaging containers by contacting the primary packaging container at a first longitudinal position of the primary packaging container; and a plurality of holding elements of a further kind arranged in the secondary packaging container. For each holding element of the first kind, a holding element of the further kind is designed and arranged to restrict a movement of the primary packaging container, which is held by the holding element of the first kind, in a lateral direction of the primary packaging container at a further longitudinal position of the primary packaging container. A distance between the first longitudinal position and the further longitudinal position of the primary packaging container is D. The primary packaging container with the distance D has a length L, where $0.5 \cdot L < D < L$.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

In some exemplary embodiments provided according to the invention, a holding device for holding a plurality of primary packaging containers for pharmaceutical, medical or cosmetic compositions is provided. The holding device includes a secondary packaging container which is designed and arranged for accommodating the plurality of primary packaging containers. A plurality of holding elements of a first kind and a plurality of holding elements of a further kind are arranged in the secondary packaging container. Each holding element of the first kind is designed and arranged to, for example non-destructively, detachably hold a primary packaging container of the plurality of primary packaging containers by contacting the primary packaging container at a first longitudinal position of the primary packaging container. For each holding element of the first kind, a holding element of the further kind is designed and arranged to restrict a movement of the primary packaging container, which is held by the holding element of the first kind, in a lateral direction of the primary packaging container, such as in all lateral directions of the primary packaging container, at a further longitudinal position of the primary packaging container. A distance between the first longitudinal position and the further longitudinal position of the primary packaging container is D. The primary packaging container with the distance D has a length L with $0.5 \cdot L < D < L$, such as $0.6 \cdot L < D < 0.99 \cdot L$, $0.7 \cdot L < D < 0.96 \cdot L$, $0.8 \cdot L < D < 0.93 \cdot L$, or $0.85 \cdot L < D < 0.9 \cdot L$.

A longitudinal direction is the direction of the length of the respective primary packaging container. Accordingly, the first and further longitudinal positions are different positions along the length of the respective primary packaging container. All lateral directions are perpendicular to the length of the respective primary packaging container. Accordingly, the terms "longitudinal" and "lateral" are based on the respective primary packaging container. Herein, the direction of the length of a primary packaging container is the direction in which the container has its greatest extension.

Each holding element of the first kind is designed and arranged to, for example non-destructively, detachably hold a primary packaging container of the plurality of primary packaging containers by contacting the primary packaging container at a first longitudinal position of the primary packaging container. A primary packaging container is non-destructively detachably held by a holding element if the container can be withdrawn from this holding device without damaging the container and, in some embodiments, also without damaging the holding device. Here, holding implies, in particular, holding in place against gravitational force. Thus, each holding element of the first kind is designed and arranged to, for example non-destructively, detachably hold a primary packaging container such that it stays in place in the secondary packaging container if the holding device is oriented upright and no external force, except for gravitation, acts on the holding device and the primary packaging container.

In some embodiments, the secondary packaging container includes a container opening and a container base which is opposite to the container opening.

In some embodiments, the holding elements of the first and furthers kinds are designed and arranged such that, for each holding element of the first kind, a holding element of the further kind is designed and arranged to prevent deflection of the primary packaging container, which is held by the holding element of the first kind, from an equilibrium orientation by more than 10°, such as more than 8°, more than 6°, or more than 2°. In some embodiments, each holding element of the first kind is designed and arranged to, for example non-destructively, detachably hold a primary packaging container such that it stays in its equilibrium orientation in the secondary packaging container if the holding device is oriented upright and no external force, except for gravitation, acts on the holding device and the primary packaging container. Thus, the equilibrium orientation is an orientation of a primary packaging container which this primary packaging container assumes if being held by one of the first holding elements of the first kind and if, at the same time, the holding device is oriented upright and no external force, except for gravitation, acts on the holding device and the primary packaging container. An exemplary equilibrium orientation is vertical.

In some embodiments, the holding elements of the first and furthers kinds are designed and arranged such that for each of the primary packaging containers which is, for example non-destructively, detachably held by one of the holding elements of the first kind there is a holding element of the further kind which, around a circumference of the primary packaging container at its further longitudinal position, has a distance to this primary packaging container in the range from 0.01 to 1.00 mm, such as from 0.02 to 0.90 mm, from 0.03 to 0.60 mm, from 0.04 to 0.40 mm, or from 0.05 to 0.20 mm.

In some embodiments, the plurality of holding elements of the first kind is arranged at or on a first plate-like element. Here, the holding elements of the first kind are, for example, openings, such as through-holes, in the first plate-like element. Alternatively, the plurality of holding elements of the first kind is in one piece with the container base. In the latter case, the holding elements of the first kind are, for example, recesses in the container base or cup-shaped receptables which are formed by the container base.

In some embodiments, the holding elements of the first kind form a first regular pattern in a plane of greatest extension of the first plate-like element and the holding elements of the further kind form a further regular pattern in a further plane. The first regular pattern may be congruent with the further regular pattern. The further plane may be parallel to the plane of greatest extension of the first plate-like element or to the container base or both. An exemplary further plane is a plane of greatest extension of the further plate-like element as defined further herein. An exemplary regular pattern forms an array which consists of rows and columns which are, for example, perpendicular to one another. A regular pattern is a pattern which is formed by identical repetition of an element in two dimensions.

In some embodiments, the plurality of holding elements of the further kind is arranged on a side of the plurality of holding elements of the first kind which is opposite to the container opening or opposite to the container base.

In some embodiments, the plurality of holding elements of the further kind is arranged at or on a further plate-like element. This may be the case if the plurality of holding elements of the first kind is arranged at or on a first plate-like element or in one piece with the container base. Here, the holding elements of the further kind are, for example, openings, such as through-holes, in the further plate-like element.

In some embodiments, the plurality of holding elements of the further kind is in one piece with the container base. Here, the plurality of holding elements of the first kind is, for example, arranged at or on a first plate-like element. Here, the holding elements of the further kind are, for example, recesses in the container base or cup-shaped receptables which are formed by the container base.

In some embodiments, for each holding element of the first kind, a holding element of the further kind is designed and arranged to restrict a movement of the primary packaging container, which is being held by the holding element of the first kind, such that D is prevented from decreasing by more than 20%, such as by more than 10%, by more than 5%, by more than 3%, or by more than 1%. The preceding movement is, for example, in a longitudinal direction, such as towards the container base. In some embodiments, for each holding element of the first kind, a holding element of the further kind is designed and arranged to restrict a movement of the primary packaging container, which is being held by the holding element of the first kind, such that D increases by the movement of the primary packaging container. In some embodiments, each holding element of the first kind is designed and arranged to form a first positive fit with a primary packaging container of the plurality of primary packaging containers, which is being held by the respective holding element of the first kind, against a movement of this primary packaging container in a longitudinal direction, wherein, for each holding element of the first kind, a holding element of the further kind is designed and arranged to form a further positive fit with the primary packaging container of the plurality of primary packaging containers, which is being held by the respective holding element of the first kind, against the movement of this primary packaging container in the longitudinal direction. The preceding holding element of the further kind is, for example, the holding element of the further kind which restricts movement of the primary packaging container in the lateral direction. In some embodiments, the first and further positive fits together prevent D from decreasing by more than 20%, such as by more than 10%, by more than 5%, by more than 3%, or by more than 1%. The above longitudinal direction is, for example, towards the container base.

In some embodiments, each holding element of the first kind is designed and arranged to, for example non-destructively, detachably hold a primary packaging container of the plurality of primary packaging containers by a positive fit, or a frictional fit, or a combination of both. An exemplary positive fit is a positive fit with a first end part or further end part or both of a primary packaging container.

In some embodiments, each of the primary packaging containers includes, in the following sequence along its length:
a. a first end part, including a discharge orifice,
b. a body part, and
c. a further end part.

In some embodiments, the body part is of cylindrical shape. In case of a container which is a syringe, the body part of cylindrical shape is often referred to as barrel.

In some embodiments, the further end part is a standing base, or includes a further orifice, or both. An exemplary container, the further end part of which is a standing base, is a vial or a cartridge. An exemplary container, the further end part of which includes a further orifice, is a syringe. In some embodiments, the discharge orifice of a container has an orifice area which is less than an orifice area of the further orifice of the same container. An exemplary further orifice is designed to accommodate a plunger.

In some embodiments, for each of the primary packaging containers, an area of the further orifice is more than an area of the discharge orifice.

In some embodiments, the further end part further includes a rim which projects laterally from the body part and at least partially, such as fully, hems the further orifice.

In some embodiments, the holding elements of the first and further kinds are designed and arranged such that the further end part of each primary packaging container faces the container opening or the container base, when the respective primary packaging container is, for example non-destructively, detachably held by one of the holding elements of the first kind.

In some embodiments, the first end part of each of the primary packaging containers includes a connecting element, the connecting element including a thread for connecting an auxiliary part to the primary packaging container. An exemplary auxiliary part is one selected from the group consisting of a needle, a nozzle, and a tubing, or a combination of at least two therefore. An exemplary needle is a hypodermic needle.

In some embodiments, the first end part of each of the primary packaging containers includes a male part of a taper fitting. An exemplary taper fitting is a Luer taper. Generally, the Luer taper may include a thread or not.

In some embodiments, the male part of the taper fitting includes a thread. In some embodiments, the thread is arranged in a sleeve.

In some embodiments, for each of the primary packaging containers, throughout the body part a thickness of a container wall is in a range from ±0.3 mm, such as ±0.2 mm, ±0.15 mm, ±0.1 mm, or ±0.08 mm, in each case based on a mean value of the thickness of the container wall in the body part of the respective primary packaging container.

In some embodiments, for each of the primary packaging containers, throughout the body part a thickness of a container wall is in a range from 0.2 to 3 mm, such as from 0.3 to 2.5 mm or from 0.4 to 2.2 mm. In some embodiments, for each of the primary packaging containers, throughout the body part a thickness of a container wall is in a range from 1.0 to 1.1 mm. In some embodiments, for each of the primary packaging containers, throughout the body part a thickness of a container wall is in a range from 1.4 to 1.8 mm. In some embodiments, for each of the primary packaging containers, throughout the body part a thickness of a container wall is in a range from 0.6 to 2.0 mm.

In some embodiments, each of the primary packaging containers has a container interior with a volume in a range from 0.5 to 100 mL, such as from 1 to 100 mL, from 1 to 50 mL, from 1 to 10 mL, or from 2 to 10 mL.

In some embodiments, the primary packaging containers are selected from the group consisting of vials, syringes, cartridges, and ampoules, or a combination of at least two thereof. An exemplary cartridge is designed for being used as a reservoir in a, for example portable, medical device. An exemplary portable medical device is an insulin pump.

In some embodiments, each of the primary packaging containers includes a container wall which at least partially surrounds a container interior, wherein the container wall comprises, for example consists of, a glass, or a polymer, or both.

In some embodiments, the polymer is a cyclic olefin copolymer (COC), or a cycloolefin polymer, or a mixture thereof.

In some embodiments, the glass is of a type selected from the group consisting of a borosilicate glass, such as a type I glass; an aluminosilicate glass; and fused silica; or of a combination of at least two thereof.

In some embodiments, the plurality of primary packaging containers consists of 4 to 500, such as 9 to 400, 12 to 300, 16 to 200, 16 to 160, 16 to 100, 16 to 90, 16 to 80, 16 to 70, 16 to 60, or 16 to 50, primary packaging containers.

In some embodiments, the holding device includes the plurality of primary packaging containers.

In some exemplary embodiments provided according to the invention, an arrangement includes the previously described holding device and the plurality of primary packaging containers. Each of the primary packaging containers is, for example non-destructively, detachably held by one of the holding elements of the first kind by contacting the primary packaging container at a first longitudinal position of the primary packaging container. A movement of each primary packaging container in a lateral direction of the primary packaging container, for example in all lateral directions of the primary packaging container, is limited by one of the holding elements of the further kind at a further longitudinal position of the of the primary packaging container. A distance between the first longitudinal position of each of the primary packaging containers and the further longitudinal position of the same primary packaging container is D. The primary packaging container with the distance D has a length L where $0.5 \cdot L < D < L$, such as $0.6 \cdot L < D < 0.99 \cdot L$, $0.7 \cdot L < D < 0.96 \cdot L$, $0.8 \cdot L < D < 0.93 \cdot L$, or $0.85 \cdot L < D < 0.9 \cdot L$.

In some embodiments, deflection of each of the primary packaging containers from an equilibrium orientation by more than 10°, such as more than 8°, more than 6°, or more than 2°, is prevented, in each case by one of the holdings elements of the first kind and one of the holdings elements of the further kind.

In some embodiments, each of the primary packaging containers has, around a circumference of the respective primary packaging container at its further longitudinal position, a distance to one of the holding elements of the further kind in the range from 0.01 to 1.00 mm, such as from 0.02 to 0.90 mm, from 0.03 to 0.60 mm, from 0.04 to 0.40 mm, or from 0.05 to 0.20 mm.

In some embodiments, the secondary packaging container is closed by a lid which is joined to the secondary packaging container. An exemplary lid is a multi-layer sheet. Additionally or alternatively, the lid may be gas-permeable. In some embodiments, the lid has been joined to the secondary packaging container by adhesively bonding or by sealing the lid to the secondary packaging container. In the case of sealing, the joint is created by a liquid and its solidification. Here, a hotmelt may be used. In the case of adhesive bonding, chemical bonds which create the joint are formed between the interfaces or surfaces of the two articles to be joined.

In some embodiments, the arrangement further includes a, for example closed, outer packaging, where the secondary packaging container is arranged in the outer packaging. Additionally or alternatively, the primary packaging containers have been decontaminated, for example sterilized. In some embodiments, the arrangement has been decontaminated, for example sterilized. In the context of the present application, decontamination is defined as an umbrella term for reducing the amount of microbes and biological agents, such as fungi, bacteria, viruses, spore forms, prions, unicellular eukaryotic organisms, etc. The special terms disinfection and sterilization differ in the amount of reduction of these. While disinfection only reduces the amount of said contaminants, sterilization effectively kills, deactivates, or eliminates all forms of life and other biological agents which are present, i.e. a reduction of 100%. Hence, disinfection is less effective than sterilization.

An exemplary outer packaging is a pouch, for example made from a plastic film. Additionally or alternatively, the outer packaging may provide a barrier against a permeation of an inert gas. Additionally or alternatively, the outer packaging may be hermetically sealed. Additionally or alternatively, the outer packaging may be less permeable for the inert gas than the lid. The outer packaging may provide a barrier action against a permeation of the inert gas, whereas the lid is permeable for the inert gas.

In some embodiments, the outer packaging includes an atmosphere which comprises an inert gas at a proportion of at least 50 vol.-%, such as at least 60 vol.-%, at least 70 vol.-%, at least 80 vol.-%, at least 90 vol.-%, or at least 95 vol.-%, in each case based on a volume of the atmosphere.

In some exemplary embodiments provided according to the invention, a use of the previously described arrangement is provided for storage of the primary packaging containers, transport of the primary packaging containers or filling of the primary packaging containers with one, selected from the group, consisting of a pharmaceutical composition, a medical composition, and a cosmetic composition, or with a combination of at least two thereof.

Features described for some embodiments provided according to the invention, for example according to the holding device, may be analogously provided in other embodiments provided according to the invention.

Primary Packaging Container

The primary packaging container, provided according to the invention, for pharmaceutical, medical or cosmetic compositions may have any size or shape which the skilled person deems appropriate in the context of the invention. Herein, a container is a primary packaging container if it intended to directly accommodate the packaging good. In particular, the primary packaging containers as referred to herein are designed to accommodate a pharmaceutical, medical or cosmetic composition in such a way that the inner side of the container wall, i.e. the side of the container wall which faces the container interior, is in direct contact with the pharmaceutical, medical or cosmetic composition. In some embodiments, a first end part of the primary packaging container includes a discharge orifice, which allows for discharging a pharmaceutical, medical or cosmetic composition from the container interior of the primary packaging container. In that case, the container wall of the primary packaging container encloses the container interior only partially. An exemplary primary packaging container is a glass container, a wall of glass (container wall) of which at least partially encloses a container interior. In some embodiments, the wall of glass is of a one-piece design. The wall of glass may be made by blow molding a glass melt; or by preparing a tube of a glass, for example in form of a hollow cylinder, forming the bottom of the primary packaging container from one end of the tube, thereby closing the tube at this end, and forming the top region of the primary packaging container from the opposite end of the tube. In some embodiments, the wall of glass is transparent. The container wall of another exemplary primary packaging container is made from a polymer. In that case, the container wall may also be transparent.

For the use herein, the volume of the container interior (also referred to as interior volume) represents the full volume of the interior of the container. This volume may be determined by filling the interior of the container with water up to the brim and measuring the volume of the amount of water which the interior can take up to the brim. Hence, the interior volume as used herein is not a nominal volume as it is often referred to in the technical field of pharmacy. This nominal volume may, for example, be less than the interior volume by a factor of about 0.5.

Besides a vial, a cartridge and an ampoule, an exemplary primary packaging container is a syringe. In some embodiments, all of the primary packaging containers of the plurality of primary packaging containers are of the same type of container, which may be selected from the precedingly mentioned types of primary packaging containers. An exemplary syringe is made from glass or polymer. An exemplary syringe, additionally or alternatively, has a length L in the range from 20 to 200 mm, such as from 25 to 190 mm, from 30 to 180 mm, or from 40 to 170 mm. Additionally or alternatively, an exemplary syringe has an interior volume in the range from 0.5 to 100 mL, such as from 0.5 to 80 mL or from 0.5 to 60 mL. Additionally or alternatively, an exemplary syringe comprises a body part which is cylindrical. This is also referred to as barrel. An exemplary barrel of a syringe has a diameter in the range from 5 to 50 mm, such as from 6 to 45 mm, from 8 to 40 mm, or from 9 to 35 mm. In some embodiments, the barrel is made from a glass or a polymer.

Glass

The container wall of each primary packaging container of the plurality of primary packaging containers may comprise a glass, for example essentially consist of the glass. This glass may be any type of glass and may have any composition which the skilled person deems suitable in the context of the invention. In some embodiments, the glass is suitable for pharmaceutical packaging. In some embodiments, the glass is of type I in accordance with the definitions of glass types in section 3.2.1 of the European Pharmacopoeia, $7^{th}$ edition from 2011. Additionally or alternatively to the preceding, the glass may be selected from the group consisting of a borosilicate glass, an aluminosilicate glass, and fused silica; or a combination of at least two thereof. For the use herein, an aluminosilicate glass is a glass which has a content of $Al_2O_3$ of more than 8 wt.-%, such as more than 9 wt.-% or in a range from 9 to 20 wt.-%, in each case based on the total weight of the glass. An exemplary aluminosilicate glass has a content of $B_2O_3$ of less than 8 wt.-%, such as at maximum 7 wt.-% or in a range from 0 to 7 wt.-%, in each case based on the total weight of the glass. For the use herein, a borosilicate glass is a glass which has a content of $B_2O_3$ of at least 1 wt.-%, such as at least 2 wt.-%, at least 3 wt.-%, at least 4 wt.-%, at least 5 wt.-%, or in a range from 5 to 15 wt.-%, in each case based on the total weight of the glass. An exemplary borosilicate glass has a content of $Al_2O_3$ of less than 7.5 wt.-%, such as less than 6.5 wt.-% or in a range from 0 to 5.5 wt.-%, in each case based on the total weight of the glass. In some embodiments, the borosilicate glass has a content of $Al_2O_3$ in a range from 3 to 7.5 wt.-%, such as in a range from 4 to 6 wt.-%, in each case based on the total weight of the glass.

A glass which is provided according to the invention may be essentially free from B. Therein, the wording "essentially free from B" refers to glasses which are free from B which has been added to the glass composition on purpose. This means that B may still be present as an impurity, but at a proportion of not more than 0.1 wt.-%, such as not more than 0.05 wt.-%, in each case based on the weight of the glass.

Holding Device

The holding device provided according to the invention may, generally, be any device which, for the skilled person, comes into consideration for holding the plurality of primary packaging containers by the plurality of holding elements of the first ad further kinds. In some embodiments, one selected from the list consisting of the secondary packaging container, the first plate-like element, and the further plate-like element, or a combination of at least two thereof has been prepared by deep drawing or molding, for example injection molding. Additionally or alternatively, one selected from the list consisting of the secondary packaging container, the first plate-like element, and the further plate-like element, or a combination of at least two thereof may be made from one or more plastics.

First and Further Plate-Like Elements

The first and further plate-like elements of the holding device may be of any plate-like shape or material which the skilled person deems appropriate in the context of the invention. In any case, the first and further plate-like elements are of plate-like shape which means that each of a length and a width of the respective element is more at least by a factor of 3, such as a factor of 5, a factor of 10, or a factor of 20, than a thickness of the plate-like element. Additionally, two opposite faces of largest area of the plate-like element are, for example, essentially parallel to each other. In some embodiments, the first plate-like element or the further plate-like element or each of both is made from one or more plastics. Additionally or alternatively, the first plate-like element or the further plate-like element or each of both may have a shore A hardness of at least 80, such as at least 90. The first plate-like element is not in one piece with the further plate-like element. Neither the first plate-like element nor the further plate-like element is in one piece with the container base, for example the secondary packaging container. In some embodiments, the secondary packaging container, for example the secondary packaging container wall, is designed and arranged to support the first plate-like element or the further plate-like element or both.

Holding Elements of the First and Further Kinds

The holding elements of the first and further kinds may, generally, be of any design which, for the skilled person, comes into consideration for holding the plurality of primary packaging containers to the holding device. The holding elements of the first kind are neither identical nor in one piece with the holding elements of the further kind. Exemplary holding elements of the first kind have been manufactured in one piece with the first plate-like element or with the secondary packaging container, for example with the container base of the secondary packaging container. Exemplary holding elements of the further kind have been manufactured in one piece with the further plate-like element or with the secondary packaging container, for example with the container base of the secondary packaging container. Additionally or alternatively, the holding elements of the first kind or the holding elements of the further kind or both together may be designed and arranged to hold the plurality of primary packaging containers by a positive fit or by a frictional fit or by both. In some embodiments, the positive fit holds the primary packaging containers against the gravitational force if the holding device is positioned upright. In some embodiments, establishing a positive fit includes elastically deforming the respective holding element of the first or further kind. Here, the respective holding element may be a clip.

Each of the plurality of holding elements of the first kind, for example comprises a receptable of a first kind. An exemplary receptable of the first kind is a through-hole, a recess or a cup-shaped receptable. Each of the plurality of holding elements of the further kind, for example comprises a receptable of a further kind. An exemplary receptable of the further kind is a through-hole, a recess or a cup-shaped receptable. An exemplary through-hole has a circular cross section. An exemplary through-hole is of a cylindrical shape.

This means that a lateral surface of the through-hole is a cylinder shell surface. The holding device may comprise 4 to 500, such as 9 to 400, 12 to 300, 16 to 200, 16 to 160, 16 to 100, 16 to 90, 16 to 80, 16 to 70, 16 to 60, or 16 to 50, holding elements of the first kind. Additionally or alternatively, the holding device may comprise 4 to 500, such as 9 to 400, 12 to 300, 16 to 200, 16 to 160, 16 to 100, 16 to 90, 16 to 80, 16 to 70, 16 to 60, or 16 to 50, holding elements of the further kind. An exemplary holding device comprises the same number of holding elements of the first and further kinds. Additionally or alternatively, the holding device of the inventions may be configured for holding 4 to 500, such as 9 to 400, 12 to 300, 16 to 200, 16 to 160, 16 to 100, 16 to 90, 16 to 80, 16 to 70, 16 to 60, or 16 to 50, primary packaging containers.

Secondary Packaging Container

As the secondary packaging container any container which the skilled person deems suitable in the context of the invention comes into consideration. The secondary packaging container comprises, for example consists of, a secondary packaging container wall, which at least partially surrounds a secondary packaging container interior. The holding elements of the first and further kinds are arranged in the secondary packaging container interior. If the primary packaging containers are held by the holding elements of the first kind, the primary packaging containers are also arranged in the secondary packaging container interior. This holds particularly in the case of the arrangement provided according to the invention. The secondary packaging container wall, may comprise or consist of, a secondary packaging container polymer. The secondary packaging container polymer is, for example, one, selected from the group, consisting of a polycondensation polymer, such as polyethylene terephthalate; a polyacrylate, such as polymethylmethacrylate; and a polyolefin, such as polypropylene or polyethylene; or a combination of at least two thereof. An exemplary secondary packaging container is tub-shaped. Additionally or alternatively, the secondary packaging container may be obtainable by deep drawing.

Pharmaceutical and Cosmetic Composition

In the context of the invention, every pharmaceutical composition and every cosmetic composition which the skilled person deems suitable comes into consideration. A pharmaceutical composition is a composition comprising at least one pharmaceutically active ingredient. An exemplary pharmaceutically active ingredient is a vaccine. A cosmetic composition is a composition comprising at least one cosmetically active ingredient. An exemplary cosmetically active ingredient is hyaluronic acid or botulinum toxin. The pharmaceutical or cosmetic composition may be fluid or solid or both. An exemplary solid composition is granular such as a powder, a multitude of tablets or a multitude of capsules. A further exemplary pharmaceutical or cosmetic composition is a parenterialium, i.e. a composition which is intended to be administered via the parenteral route, which may be any route which is not enteral. Parenteral administration can be performed by injection, e.g. using a needle (usually a hypodermic needle) and a syringe, or by the insertion of an indwelling catheter.

Test Methods

The following test methods are to be used in the context of the invention. Unless otherwise specified, the measurements have to be carried out at an ambient temperature of 23° C., an ambient air pressure of 100 kPa (0.986 atm) and a relative atmospheric humidity of 50%.

Wall Thickness and Tolerance of Wall Thickness

The wall thickness and deviations from the mean value of the wall thickness (tolerance) are determined in accordance with the following standards for the respective type of container:
  DIN ISO 8362-1 for vials,
  DIN ISO 9187-1 for ampoules,
  DIN ISO 110 4 0-4 for syringes,
  DIN ISO 13926-1 for cylindrical cartridges, and
  DIN ISO 11040-1 for dental cartridges.

Transport Simulation

The transport simulation is conducted in accordance with ASTM D4169-16. In particular, the transport simulation consists of 2 sequences which are performed with the same sample one after the other. The environmental conditions in the test room are:
  temperature: in the range from 15 to 35° C.
  relative humidity: <85%
  air pressure: in the range from 860 to 1060 hPa Sample The sample is pallet unit which consists of a wooden pallet on which boxes of corrugated cardboard are stacked such that the overall dimensions of the sample are
  length: 1200 mm,
  width: 800 mm and
  height: 940 mm.

The boxes are tightly secured to each other by plastic stretch foil. Each of the boxes is filled with identical arrangements of the kind of arrangement to be tested. The boxes do not contain any additional filling material. Accordingly, each arrangement consists of a holding device which is fully loaded with identical empty containers.

First Sequence

The first sequence is conducted in accordance with schedule A—Mechanical Handling—Unitized Loads as described in section 10.3.2 of ASTM D4169-16. A rotational flat drop test in accordance with ASTM D6179, method C is conducted. The drop height is selected from the table in section 10.3.2.3 of ASTM D4169-16 based on the assurance level II. The test consists of 1 drop from each opposite base edge of the sample. One edge of the sample is supported by the floor. The other side is raised up to the drop height and released to fall flat on the impact surface (bottom of the wooden pallet). This procedure is performed with each opposite base edge which results in 4 drops altogether. The following test steps are performed:
  1. Support edge 3-6 and raise edge 3-5; drop on face 3
  2. Support edge 3-5 and raise edge 3-6 drop on face 3
  3. Support edge 2-3 and raise edge 3-2; drop on face 3
  4. Support edge 3-4 and raise edge 3-4; drop on face 3

If any of the boxes of the sample has moved one the pallet in one of the preceding steps 1. to 3., it is pushed back into place before the subsequent step. At the end of step 4, all boxes are pushed back to their original place on the pallet.

Second Sequence

The second sequence is conducted in accordance with schedule D—Stacked—Vibration as described in section 12.2 of ASTM D4169-16. A random vibration test in accordance with ASTM D4728 is conducted. In the test, the sample is in normal shipping orientation, i.e. with the wooden pallet at the bottom. The sample is loaded in accordance with section 11.4 of ASTM D4169-16. The top load TL is calculated from formula (3) as given in section 11.4 of ASTM D4169-16. Therein, H=2.7 m and F=1. Further parameters of the second sequence are:
  Truck Loop Profile:
    0.40 $G_{rms}$ for 40 min 0.54 Grms for 15 min
0.70 Grms for 5 min
Numbers of Loops: 1
Duration in Total: 1 h on Face 3
Air Profile:
AL II/Grms: 1.05
Test Duration: 2 h on Face 3
Particle Load after Transport Simulation Directly after the sample has been subjected to the above transport simulation, the particle load of the exterior surfaces of the containers of the arrangement to be studied is determined in particles of a specific size range (particle class) per $cm^2$ of the sum of the surface areas of the exterior surfaces. Any further handling of the sample which could lead to the formation of further particles is to be avoided between the transport simulation and determination of the particle load.

Liquid Particle Counting System

The particle load of the containers of the arrangement to be studied is determined using a liquid particle counting system which includes a particle counter Pacific Scientific Hiac Royco, Model 9703 (F4-088) and a desktop computer on which runs the software PharmSpec 3.4.0 as it comes with the particle counter. Generally, the particle counter draws up the test liquid via an ascending pipe and guides it past a scattered light sensor. The signals coming from the scattered light sensor are read out and processed by the software. In this test method, only particle-free water which has been prepared by an H2O-EDI-2-T Arium® advance EDI (10 l/h) tabletop system from Sartorius AG, Gottingen, Germany is used for cleaning, for flushing and rinsing, as zero sample, for any filter exchange and for preparing the test liquid. This system is an apparatus for preparing pure water of type 2. The system has a flow performance of 10 liters per hour.

Preparation of the Particle Counter

The medium required for flushing (particle-free water) and testing (test liquid) is filled into the vessel at least 1 hour before the test. The particle counter is operated under laminar flow conditions. Prior to the start of the tests, the complete laminar flow workstation running with working flow is cleaned with a moistened particle-free cloth. The lifting arm to which the suction pipe is attached can be controlled via the control panel. Before the first measurement can be carried out, the sampler must be cleaned and adjusted so that the suction tube is immersed as deeply as possible in the test liquid without touching the bottom of the vessel. The adjustment is carried out with the vessel with which the later measurements are also carried out. The lowest position of the lifting arm is saved and then the lifting arm is moved back to the starting position. In order to clean the sampler, a vessel which has been flushed 3 times with particle-free water is filled with at least 35 mL of particle-free water and positioned under the lifting arm. The lifting arm is moved into the lower position which has been saved as described above. Again, the lifting arm must not touch the bottom of the vessel. The automatic flushing sequence is started. Per cleaning run 10 mL of liquid consumed. 4 cleaning runs are conducted. Under no circumstances should air be sucked in. Therefore, there must be at least 35 mL of particle-free water in the vessel. After cleaning, the lifting arm is moved to the upper position.

Zero Sample

Before starting the tests, the particle-free water used to prepare the test liquid must be checked for its particle content. For this purpose, the vessel which will be used for the measurements is rinsed 3 times with particle-free water. Then, the vessel is filled with 40 mL of the particle-free water as zero sample. After the zero sample has been left to stand for at least 2 minutes to deaerate, the test can be started. The particle counter measures the number of particles in a given volume of the particle-free water. Here, particles of all particle sizes possible have to be recorded. For this, the machine draws up and tests 6 times 5 mL of liquid. The first measurement is rejected. An acceptance criterion is set to a maximum of 25 particles of particle size of at least 10 μm per 25 mL of the particle-free water. If this value is not met, preparation of the particle-free water must be adapted and measurement of the zero sample must be repeated until the acceptance criterion is met.

Test Liquid

The stretch foil is removed from the cardboard boxes. The box which contains the arrangement to be studied is taken from the pallet and opened under laminar flow. All further steps are conducted under laminar flow. The arrangement to be studied is taken out of the box. A glass beaker with enough particle-free water for immersing one primary packaging container at a time to half of its length in the water in an upright orientation is prepared. In any case, a minimum of 40 mL of particle-free water is used and referred to as pool in the following. The glass beaker is flushed at least 3 times with particle-free water beforehand. All openings of the primary packaging containers of the arrangement to be studied are closed by stoppers which have been rinsed at least 3 times with particle-free water beforehand. One after the other, each of the primary packaging containers is immersed to half of its length in the pool (the same particle-free water) in an upright orientation and manually agitated to make a stirring motion while maintaining the upright orientation for 5 s. In the case of syringes, the upright orientation means that the tips of the syringes face upwards. The test liquid is the pool in which all the primary packaging containers of the arrangement have been washed as described in the preceding.

Measurement

The test liquid is filled into the vessel at least 1 hour before the test. The particle counter measures the number of particles of particle sizes of ≥2 μm, ≥5 μm, ≥10 μm, ≥15 μm, ≥25 μm, ≥50 μm, ≥75 μm and ≥100 μm. For this, the machine tests 6 times 5 mL of the test liquid and rejects the first measurement. Therefore, the minimum volume of the test liquid is 35 mL. For each of the above particle size classes, the number of particles per $cm^2$ is determined by dividing the number particles in the test liquid as determined by the particle counter by the sum of the area of the exterior surfaces of the primary packaging containers of the arrangement.

Exemplary embodiments provided according to the invention are set out in more detail below by examples and figures, with the examples and figures not denoting any restriction on the invention. Furthermore, unless otherwise indicated, the figures are not to scale.

Figure 1:
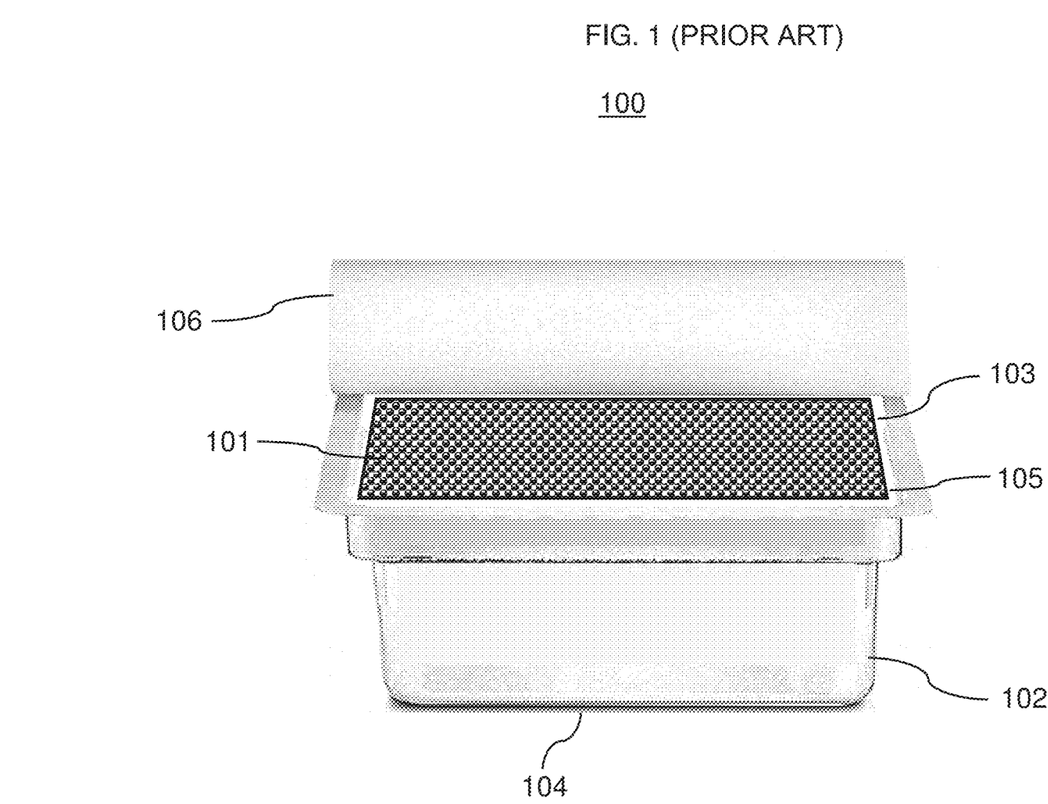
FIG. 1 illustrates a scheme of a general tub with a nest for primary packaging containers.

For each of the examples and comparative examples, syringes of a type specified below, in each case assembled with a tip cap and packed in a nest which is placed into a tub are used. The tub is covered by a Tyvek® inlay, placed in the tub and sealed with a Tyvek® seal. Each tub is packed in a double polyethylene bag. FIG. 1 shows a scheme of the general principle of tub and nest (the bag is not shown). This general principle applies to all of the examples and comparative examples.

In the examples 1 to 3 and the comparative examples 1 and 2 syringes of the type TopPac®, format is 50.0 mL from Schott AG are used. The barrels of these syringes are made from COC. The discharge orifice of each syringe is closed by a rigid polymer cap with a threaded tip of the type TopPac® Rigid Cap with a rubber tip cap of the type Datwyler FM 257. Here, 20 syringes are packed in each nest.

In the examples 4 to 6 and the comparative examples 3 and 4 syringes of the type syriQ® with Luer Cone, format 3.0 mL from Schott AG are used. The barrels of these syringes are made from FIOLAX® glass. The discharge orifice of each syringe is closed by a rigid polypropylene cap with a threaded tip of the type syriQ® Rigid Cap with a rubber tip cap of the type Datwyler FM 27. Here, 100 syringes are packed in each nest.

Different ways to hold the syringes in the nests are studied in the examples and comparative examples. These ways are described in detail further herein in the context of FIGS. 2 to 6. As depicted in the figures, the holding devices of FIGS. 4 to 6 allow packing a greater number of syringes in each nest of constant size than the holding devices of FIGS. 2 and 3. This is because, the devices of FIGS. 4 to 6 allow to arrange the syringes in a more space saving manner than the device of FIG. 3. In addition, the devices of FIGS. 4 to 6 show reduced plastic warping of the plate-like carrier elements under the load of the syringes. Nevertheless, for the purpose of comparison, in all of the examples and comparative examples which make use of the same type of syringe, the same number of syringes are used in each nest.

The below Table 1 provides an overview of the types of syringes and holding devices used in the examples and comparative examples.

TABLE 1

Figure 2:
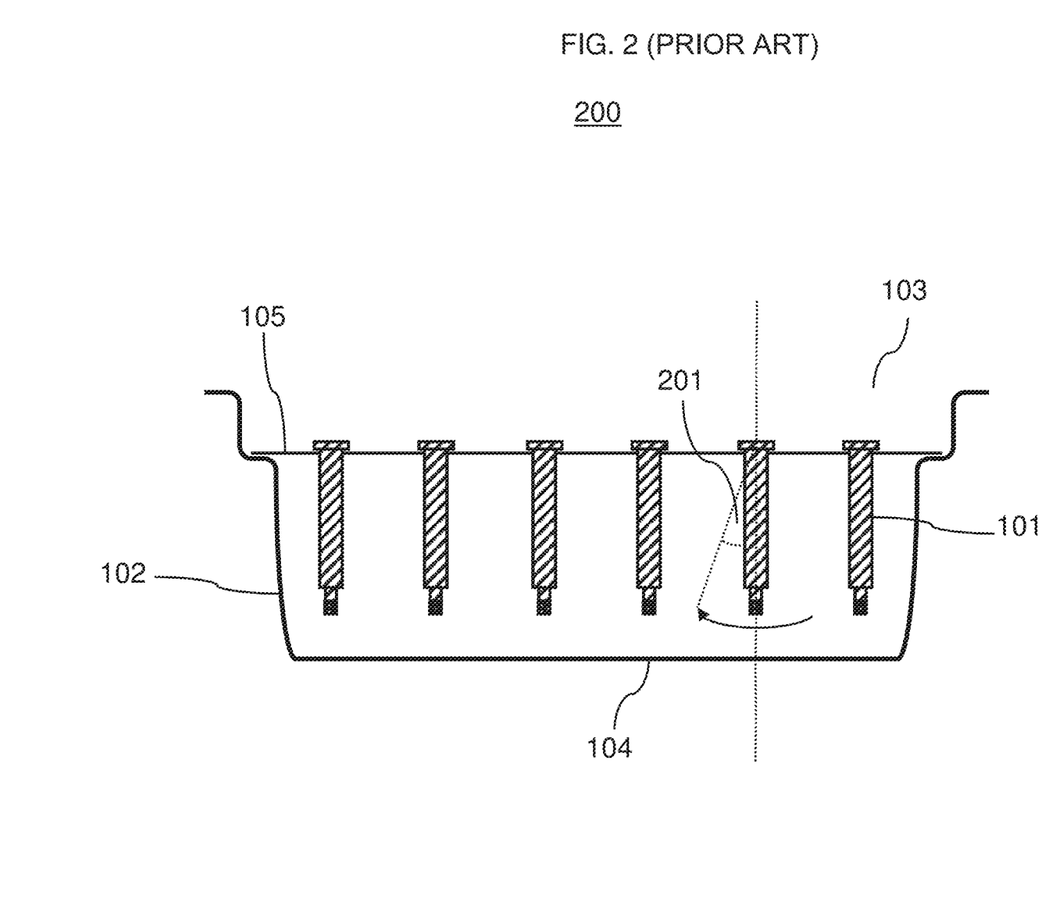
FIG. 2 illustrates an arrangement which is not provided according to the invention.
Figure 3:
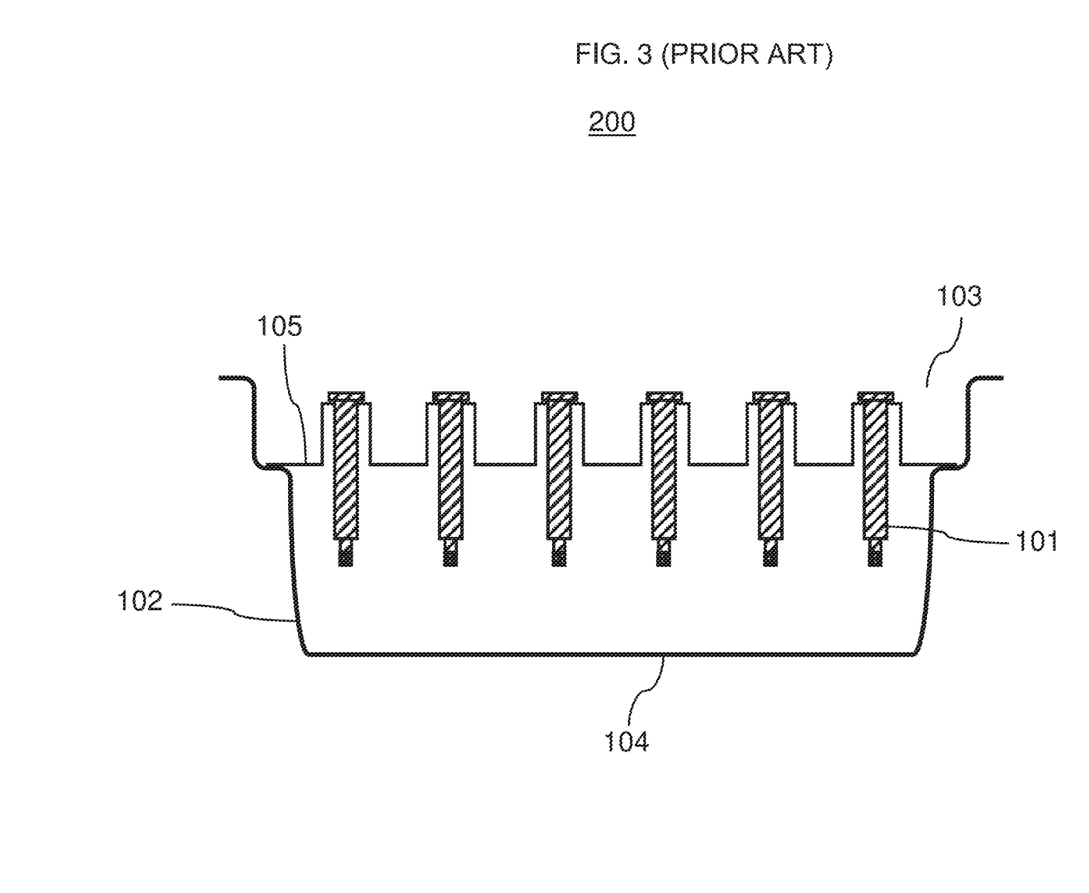
FIG. 3 illustrates a further arrangement which is not provided according to the invention.
Figure 4:
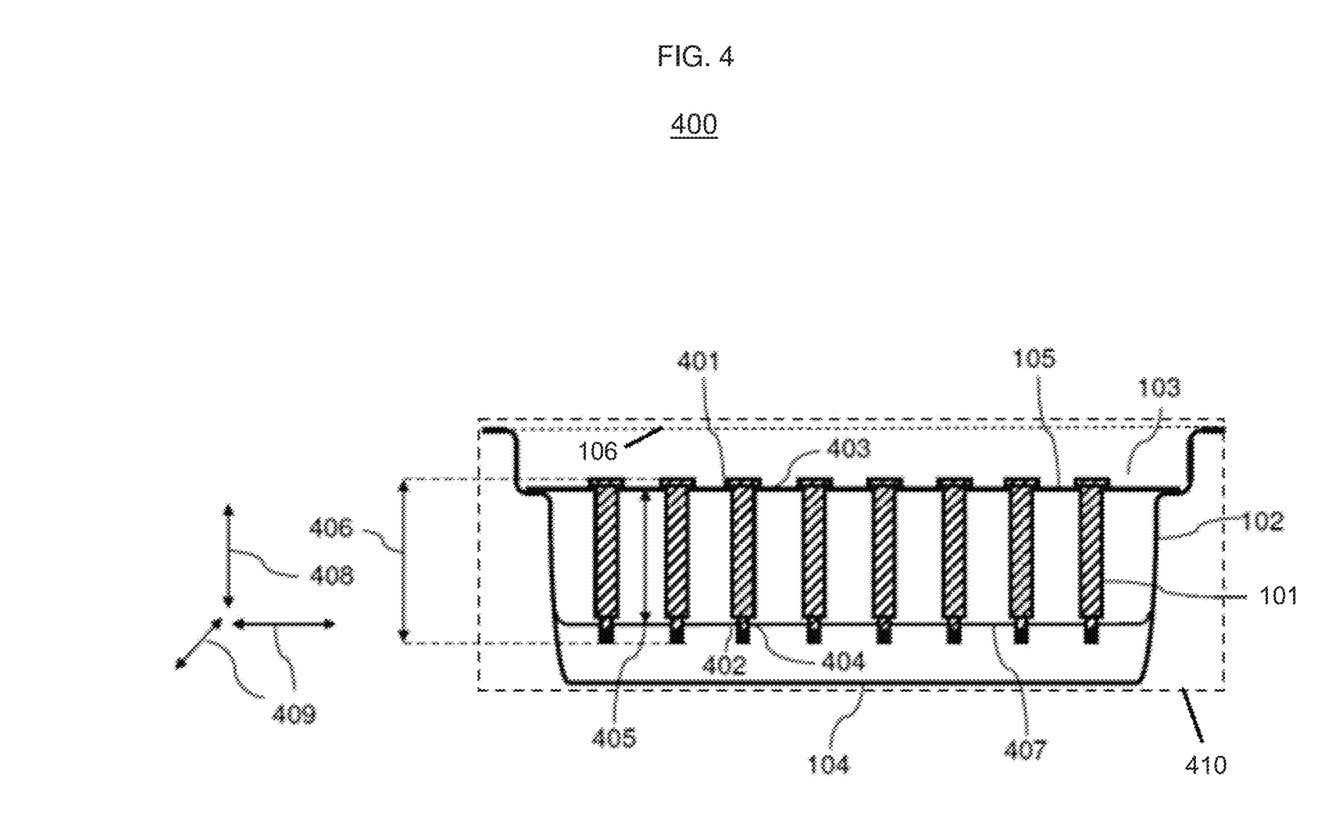
FIG. 4 illustrates an exemplary embodiment of an arrangement provided according to the invention.
Figure 5:
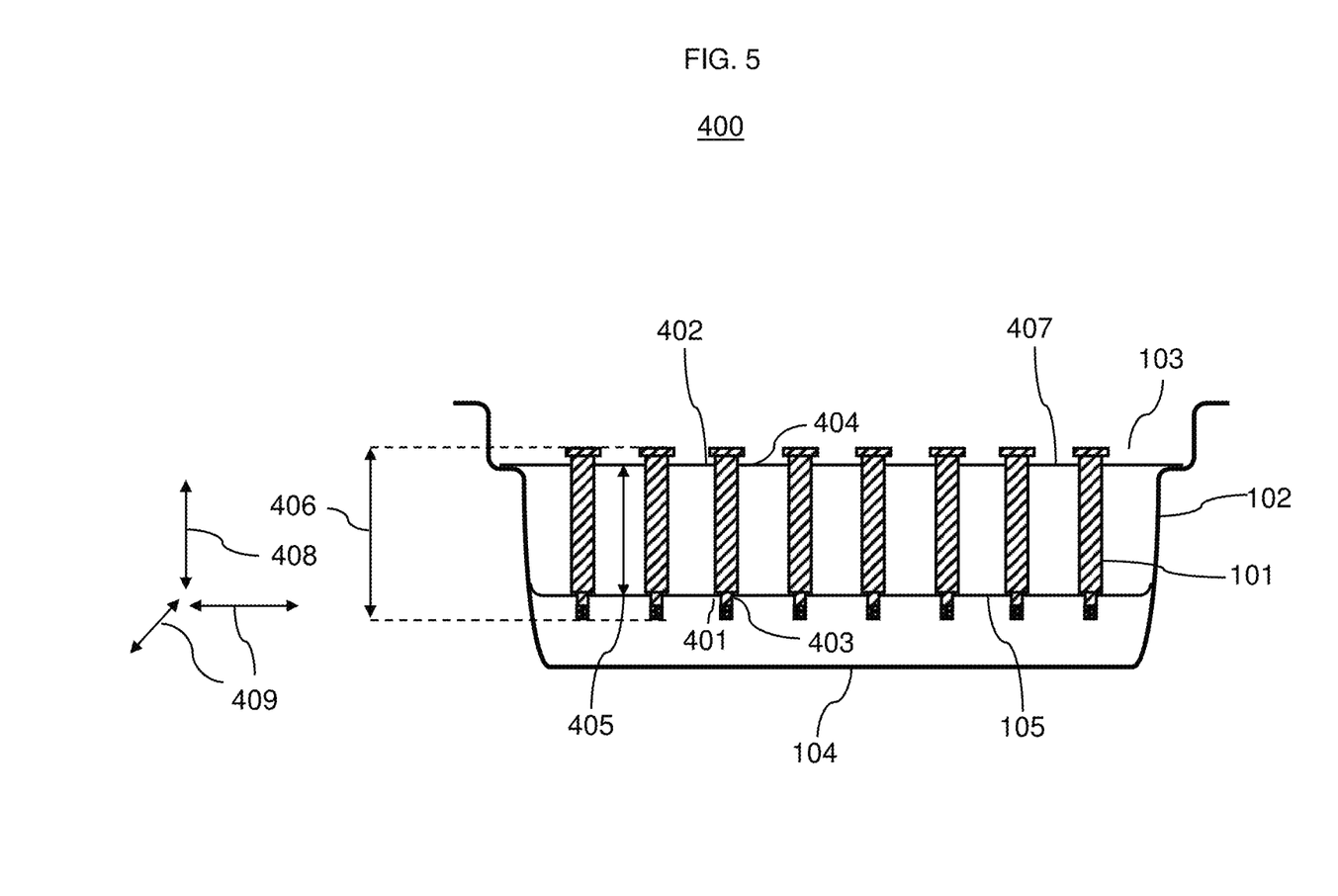
FIG. 5 illustrates an exemplary embodiment of an arrangement provided according to the invention.
Figure 6:
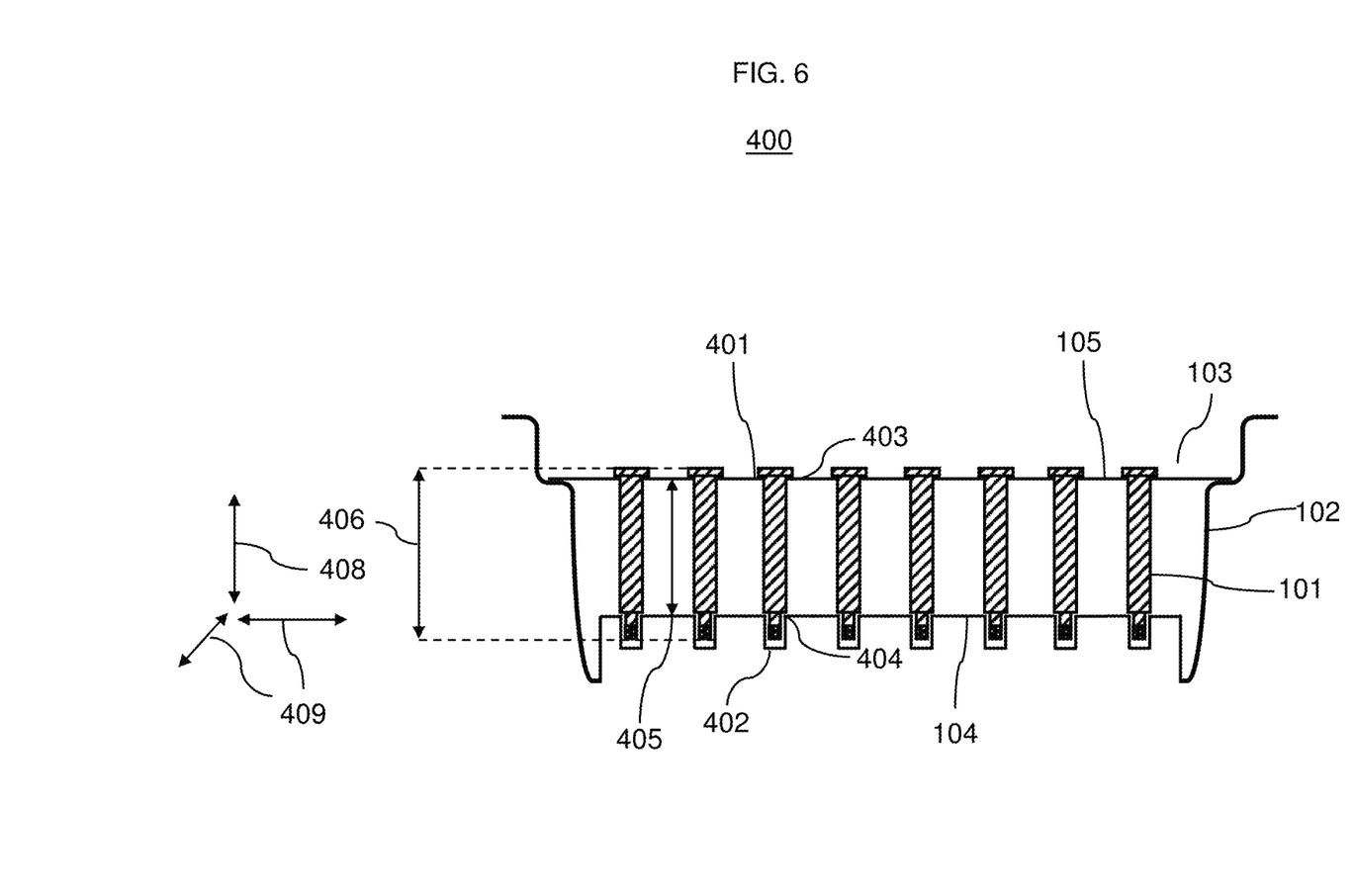
FIG. 6 illustrates an exemplary embodiment of an arrangement provided according to the invention.

| | Syringe Type | Holding Device Type |
|---|---|---|
| Example 1 | Schott TopPac ® 50.0 mL | FIG. 4 |
| Example 2 | Schott TopPac ® 50.0 mL | FIG. 5 |
| Example 3 | Schott TopPac ® 50.0 mL | FIG. 6 |
| Example 4 | Schott syriQ ® Luer Cone 3.0 mL | FIG. 4 |
| Example 5 | Schott syriQ ® Luer Cone 3.0 mL | FIG. 5 |
| Example 6 | Schott syriQ ® Luer Cone 3.0 mL | FIG. 6 |
| Comparative Example 1 | Schott TopPac ® 50.0 mL | FIG. 2 |
| Comparative Example 2 | Schott TopPac ® 50.0 mL | FIG. 3 |
| Comparative Example 3 | Schott syriQ ® Luer Cone 3.0 mL | FIG. 2 |
| Comparative Example 4 | Schott syriQ ® Luer Cone 3.0 mL | FIG. 3 |

10 closed tubs in foil bags as described previously per example and comparative example are subjected to the transport simulation as described in the test methods section. Subsequently, the syringes are carefully taken out of the tubs one by one and inspected by naked eye for an air gap between the rigid cap (TopPac® Rigid Cap or syriQ® Rigid Cap) and the Luer taper of the discharge orifice. If there is any such air gap, it can be assumed that the CCI has been broken in the transport simulation.

After having subjected further 10 closed tubs in foil bags the to the transport simulation as described in the test methods section, the particle load on the exterior surfaces of the syringes is determined as described previously in the test methods section. Here, the test liquids are prepared by washing all syringes of the 10 nests of the same example or comparative example in the same pool.

Further 10 closed tubs in foil bags of each of the examples and comparative examples are opened. Then a laser distance meter is used to precisely detect any downward bending of the plate-like carriers due to the weight of the containers.

The results of the previously described studies are summarized in Table 2 below. Therein, "++" means a more favorable result than "+" which means a more favorable result than "0" which represents a still more favorable result than "−" which depicts a still more favorable result than "−−".

TABLE 2

| | Good CCI | Low Particle Load | Good Processability |
|---|---|---|---|
| Example 1 | + | + | + |
| Example 2 | + | + | + |
| Example 3 | + | + | ++ |
| Example 4 | + | ++ | 0 |
| Example 5 | + | ++ | 0 |
| Example 6 | + | ++ | ++ |
| Comparative Example 1 | −− | − | − |
| Comparative Example 2 | − | −− | 0 |
| Comparative Example 3 | −− | 0 | −− |
| Comparative Example 4 | − | 0 | − |

In the comparative examples, the tip caps of the syringes tend to loosen due to the transport simulation. Accordingly, the microbiological barrier of the container closure (Container Closure Integrity—CCI) may be broken. This might represent a safety issue for patients to be treated with the syringes. In the examples, this is not an issue.

Further, Table 2 shows that the polymer syringes, generally, tend to produce more particles due to abrasion in the transport simulation. For glass as well as polymer syringes, the number of particles can, however, be substantially reduced in the examples with respect to the comparative examples. This is particularly important because particles can get into the interior of the syringe. Particles in the filled syringe represent a severe safety issue for patients to be treated with the syringes.

As the weight of the glass syringes is more than the weight of the polymer syringes, the carrier plates of nests with glass syringes tend to suffer from a greater downward bending than the carrier plates of nests with polymer syringes. In any case, the nests of the examples show less such bending than the nests of the comparative examples. The nests of the examples 3 and 6 do show even less plastic bending. There can be issues in processing nests, which have a curvature, by an automatic filling machine. In particular, processing failures may occur. If the downward curvature is too much, the nest may even be excluded from being processed automatically. It follows that the nests of the examples, in particular examples 3 and 6, are very much suitable for being processed by an automatic filling machine.

FIG. 1 shows a scheme of a general tub with nest for primary packaging containers 101. The tub is a secondary packaging container 102 as referred to herein. This secondary packaging container 102 comprises a container opening 103 and a container base 104 which is opposite to the container opening 103. A first plate-like element 105 forms the nest which is arranged in the tub. The first plate-like element 105 holds a plurality of primary packaging containers 101 such as syringes 101. A lid 106, which used to close the container opening 103, has been partially peeled off the secondary packaging container 102 in order to reveal the nest. An arrangement 400 provided according to the invention may have all the features of the tub with nest and primary packaging containers 101 as shown in FIG. 1.

FIG. 2 shows a cross-sectional view of an arrangement 200 which is not provided according to the invention. Here, a tub-shaped secondary packaging container 102 accommodates a first plate-like element 105 which includes a regular pattern of through-holes. The through-holes are arranged in rows and columns which form an array. Each of these through-holes holds a syringe 101 by a positive fit. FIG. 2 shows 6 syringes 101 in their vertical equilibrium orientations. Each syringe 101 which is being held in one of the through-holes can be deflected from its equilibrium orientation by a maximum angle of deflection 201 of 30°.

FIG. 3 shows a cross-sectional view of a further arrangement 200 which is not provided according to the invention. This arrangement 200 is similar to the one of FIG. 2, however, with a modified first plate-like element 105 which prevents deflection of the syringes 101, which are being held by the modified first plate-like element 105, from their equilibrium orientations by more than 20°.

FIG. 4 shows a cross-sectional view of an arrangement 400 provided according to the invention. The arrangement 400 comprises a secondary packaging container 102 which accommodates a plurality of primary packaging containers 101 which is also part of the arrangement 400. The secondary packaging container 102 may be arranged inside a closed outer packaging 410, such as a pouch, as illustrated. Here, the primary packaging containers 101 are syringes 101 of the type shown in FIG. 7. Arranged at a first plate-like element 105 is a plurality of holding elements of a first kind 401. A plurality of holding elements of a further kind 402 is arranged at a further plate-like element 407. The secondary packaging container 102, the first plate-like element 105 and the further plate-like element 407 together form a holding device provided according to the invention. The holding elements of the first kind 401 are through-holes in the first plate-like element 105, where the holding elements of the further kind 402 are through-holes in the further plate-like element 407. A first regular pattern, formed by the holding elements of the first kind 401 in a plane of greatest extension of the first plate-like element 105, is congruent with a further regular pattern as formed by the holding elements of the further kind 402 in a plane of greatest extension of the further plate-like element 407. The first 105 and further plate-like elements 407 with the holding elements of the first 401 and further kinds 402 are arranged in the secondary packaging container 102 which is a tub of the type shown in FIG. 1. Accordingly, the secondary packaging container 102 comprises a container opening 103 and a container base 104 which is opposite to the container opening 103. The first 105 and further plate-like elements 407 are supported by a wall of the secondary packaging container 102. Here, the further plate-like element 407 is arranged on a side of the first plate-like element 105 which is opposite to the container opening 103. Accordingly, the plurality of holding elements of the further kind 402 is arranged on a side of the plurality of holding elements of the first kind 401 which is opposite to the container opening 103. Each of the syringes 101 is non-destructively detachably held by one of the holding elements of the first kind 401 by contacting the respective syringe 101 at a first longitudinal position 403 of the syringe 101. A movement of each of the syringes 101 in any of its lateral directions 409 is restricted by one of the holding elements of the further kind 402 at a further longitudinal position 404 of the syringe 101. Here, the first 403 and further longitudinal positions 404 are different positions along a length L 406 of the respective syringe 101 which determines a longitudinal direction 408 of this syringe 101. If a distance 405 between the first longitudinal position 403 of each of the syringes 101 and the further longitudinal position 404 of the syringe 101 is D, then D is 0.9·L. The holding elements of the first 401 and furthers kinds 402 are designed and arranged such that, for each holding element of the first kind 401, a holding element of the further kind 402 is designed and arranged to prevent deflection of the syringe 101, which is being held by the holding element of the first kind 401, from its vertical equilibrium orientation by more than 6°. Here, D can decrease by the weight of the syringes 101 only if the first plate-like element 105 bends downwards. This is because each of the holding elements of the first kind 401 forms a first positive fit with the syringe 101, which is being held by the respective holding element of the first kind 401, against a movement of this syringe 101 in a longitudinal direction 408 towards the container base 104. After a certain degree of bending the first plate-like element 105, a holding element of the further kind 402 forms a further positive fit with the syringe 101, which is being held by the respective holding element of the first kind 401, against any further movement of this syringe 101 in the longitudinal direction 408 towards the container base 104. Even if the syringe 101 would be moved further towards the container base 104 by bending both of the first 105 and further plate-like elements 407, D would not decrease any further. Accordingly, the first and further positive fits together prevent D from decreasing by more than 20% by the movement of the respective syringe 101 in the longitudinal direction 408 towards the container base.

FIG. 5 shows a cross-sectional view of a further arrangement 400 provided according to the invention. The arrangement 400 of FIG. 5 is the same as the arrangement 400 of FIG. 4, except for the further plate-like element 407 being arranged on a side of the first plate-like element 105 which is opposite to the container base 104. Accordingly, the plurality of holding elements of the further kind 402 is arranged on a side of the plurality of holding elements of the first kind 401 which is opposite to the container base 104. Further, in FIG. 5, D is 0.7·L. Again, the secondary packaging container 102, the first plate-like element 105 and the further plate-like element 407 together form a holding device provided according to the invention. The holding elements of the first 401 and furthers kinds 402 are designed and arranged such that, for each holding element of the first kind 401, a holding element of the further kind 402 is designed and arranged to prevent deflection of the syringe 101, which is being held by the holding element of the first kind 401, from its vertical equilibrium orientation by more than 10°. If the weight of the syringes 101, here, bends the first plate-like element 105, which is the lower one of the plate-like elements 105, 407, downwards, D even increases, instead of decreasing. Each of the holding elements of the first kind 401 forms a first positive fit with the syringe 101, which is being held by the respective holding element of the first kind 401, against a movement of this syringe 101 in a longitudinal direction 408 towards the container base 104. After a certain degree of bending the first plate-like element 105, a holding element of the further kind 402 forms a further positive fit with the syringe 101, which is being held by the respective holding element of the first kind 401, against any further movement of this syringe 101 in the longitudinal direction 408 towards the container base 104. Even if the syringe 101 would be moved further towards the container base 104 by bending both of the first 105 and further plate-like elements 407, D would not change any further, in particular not decrease. Accordingly, the first and further positive fits together prevent D from decreasing at all by the movement of the respective syringe 101 in the longitudinal direction 408 towards the container base.

FIG. 6 shows cross-sectional view of a further arrangement 400 provided according to the invention. The arrangement 400 of FIG. 6 is the same as the arrangement 400 of FIG. 4 with the following exceptions. Here, the secondary packaging container 102 and the first plate-like element 105 together form a holding device provided according to the invention. The arrangement 400 of FIG. 6 lacks the further plate-like element 407. Instead, the holding elements of the further kind 402 are formed in one piece with the container base 104 of the secondary packaging container 102. More specifically, the holding elements of the further kind 402 are cup-shaped receptables formed by the container base 104. In consequence, D is 0.8·L. The holding elements of the first 401 and furthers kinds 402 are designed and arranged such that, for each holding element of the first kind 401, a holding element of the further kind 402 is designed and arranged to prevent deflection of the syringe 101, which is held by the holding element of the first kind 401, from its vertical equilibrium orientation by more than 8°. Here, D can decrease by the weight of the syringes 101 only if the first plate-like element 105 bends downwards. This is because each of the holding elements of the first kind 401 forms a first positive fit with the syringe 101, which is being held by the respective holding element of the first kind 401, against a movement of this syringe 101 in a longitudinal direction 408 towards the container base 104. After a certain degree of bending the first plate-like element 105, a holding element of the further kind 402 forms a further positive fit with the syringe 101, which is being held by the respective holding element of the first kind 401, against any further movement of this syringe 101 in the longitudinal direction 408 towards the container base 104. The syringe 101 could only be moved further in the same direction if the container base 104 would bend downwards. Even if the first plate-like element 105 and the container base 104 would bend, D would not decrease any further. Accordingly, the first and further positive fits together prevent D from decreasing by more than 3% by the movement of the respective syringe 101 in the longitudinal direction 408 towards the container base.

Figure 7:
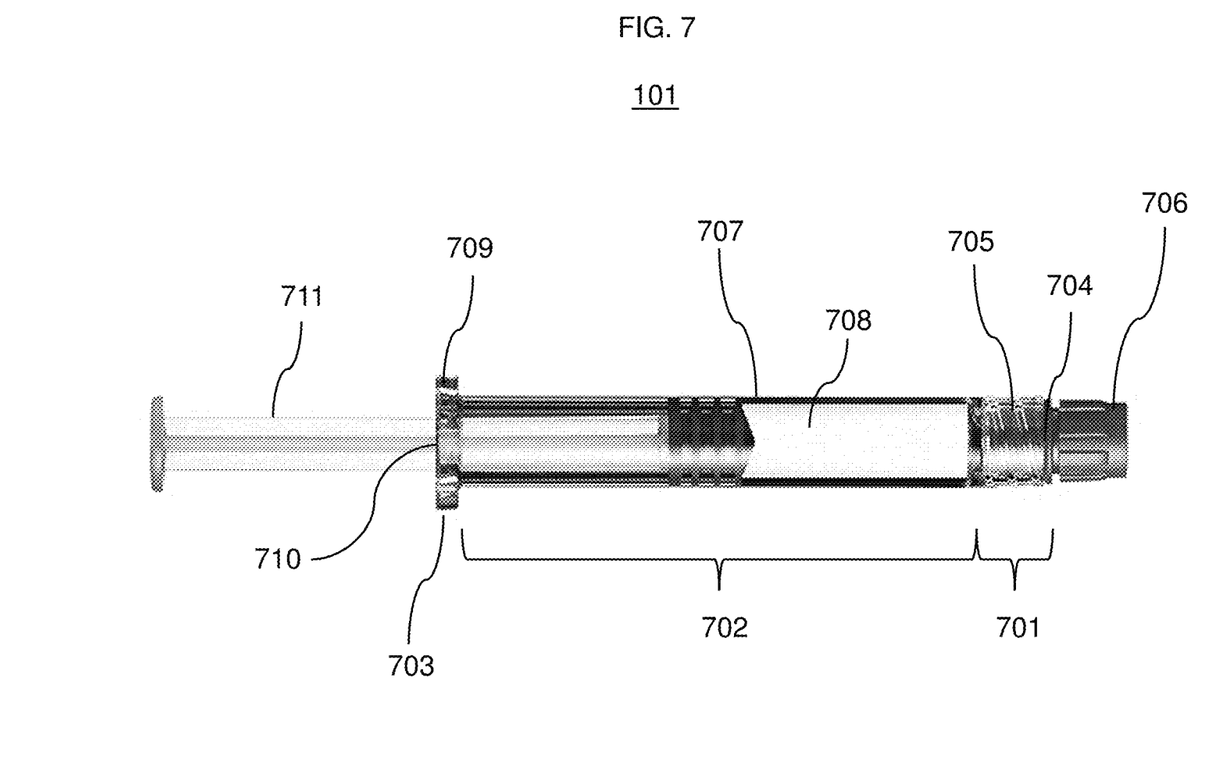
FIG. 7 shows a TopPac® syringe in 1.0 mL format from Schott AG.

FIG. 7 shows a TopPac® syringe in a 1.0 mL format from Schott AG. This syringe 101 is a primary packaging container 101 as referred to in the context of the invention. The syringe 101 comprises a container wall 707 which partially surrounds a container interior 708. The container wall 707 forms, in the following sequence from top to bottom, a first end part 701, comprising a discharge orifice 704; a body part 702; and a further end part 703. The body part 702, which in the art is also referred to as barrel, is a hollow cylinder. The further end part 703 comprises a further orifice 710. The discharge orifice 704 has an orifice area which is less than an orifice area of the further orifice 710. The further orifice 710 accommodates a plunger 711. The further end part 703 further comprises a rim, in the art also referred to as flange, which projects laterally from beyond the body part 702 and hems the further orifice 710. The container wall 707 is made from a cyclic olefin copolymer. The first end part 701 comprises a connecting element which is a male part 705 of a Luer taper. The connecting element comprises a thread for connecting a hypodermic needle to the syringe 101. The thread is arranged in a sleeve. The syringes 101 of the arrangements 400 of FIGS. 2 to 6 are syringes 101 of the type shown in FIG. 7, however, without the plunger 711.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 100 general tub with nest for primary packaging containers
101 primary packaging container/syringe
102 secondary packaging container
103 container opening
104 container base
105 first plate-like element
106 lid
200 arrangement which is not provided according to the invention
201 maximum angle of deflection from equilibrium orientation
400 arrangement provided according to the invention
401 holding element of first kind
402 holding element of further kind
403 first longitudinal position
404 further longitudinal position
405 distance D between first longitudinal position and further longitudinal position of primary packaging container
406 length L of primary packaging container
407 further plate-like element
408 longitudinal directions
409 lateral directions
410 outer packaging
701 first end part
702 body part
703 further end part
704 discharge orifice
705 male part of Luer taper
706 stopper
707 container wall
708 container interior
709 rim
710 further orifice
711 plunger

What is claimed is:

1. An arrangement, comprising:
a plurality of primary packaging containers for pharmaceutical, medical, or cosmetic compositions; and
a holding device holding the plurality of primary packaging containers, the holding device comprising:
a secondary packaging container which is designed and arranged for accommodating the plurality of primary packaging containers;
a plurality of holding elements of a first kind arranged in the secondary packaging container, each holding element of the first kind detachably holding a primary packaging container of the plurality of primary packaging containers by contacting the primary packaging container at a first longitudinal position of the primary packaging container; and
a plurality of holding elements of a further kind arranged in the secondary packaging container, wherein, for each holding element of the first kind, a holding element of the further kind limits a movement of the primary packaging container, which is held by the holding element of the first kind, in a lateral direction of the primary packaging container at a further longitudinal position of the primary packaging container, wherein a distance between the first longitudinal position and the further longitudinal position of the primary packaging container is D, wherein the primary packaging container with the distance D has a length L, wherein $0.7 \cdot L < D < L$.

2. The arrangement of claim 1, wherein the holding elements of the first kind and the holding elements of the further kind are designed and arranged such that, for each holding element of the first kind, a holding element of the further kind is designed and arranged to prevent deflection of the primary packaging container, which is held by the holding element of the first kind, from an equilibrium orientation by more than 10°.

3. The arrangement of claim 1, wherein the holding elements of the first kind and the holding elements of the further kind are designed and arranged such that for each of the primary packaging containers which is detachably held by one of the holding elements of the first kind there is a holding element of the further kind which, around a circumference of the primary packaging container at its further longitudinal position, has a distance to this primary packaging container in a range from 0.01 to 1.00 mm.

4. The arrangement of claim 1, wherein the plurality of holding elements of the first kind is arranged at or on a first plate-like element.

5. The arrangement of claim 4, wherein the holding elements of the first kind form a first regular pattern in a plane of greatest extension of the first plate-like element and wherein the holding elements of the further kind form a further regular pattern in a further plane.

6. The arrangement of claim 5, wherein the first regular pattern is congruent with the further regular pattern.

7. The arrangement of claim 1, wherein the secondary packaging container comprises a container opening and a container base which is opposite to the container opening.

8. The arrangement of claim 7, wherein the plurality of holding elements of the further kind is arranged on a side of the plurality of holding elements of the first kind which is opposite to the container opening.

9. The arrangement of claim 7, wherein the plurality of holding elements of the further kind is in one piece with the container base.

10. The arrangement of claim 1, wherein the plurality of holding elements of the further kind is arranged at or on a further plate-like element.

11. The arrangement of claim 1, wherein, for each holding element of the first kind, a holding element of the further kind is designed and arranged to restrict a movement of the primary packaging container, which is being held by the holding element of the first kind, such that D is prevented from decreasing by more than 20%.

12. The arrangement of claim 1, wherein each holding element of the first kind is designed and arranged to detachably hold a primary packaging container of the plurality of primary packaging containers by a positive fit, a frictional fit, or a combination of both.

13. The arrangement of claim 1, wherein each of the primary packaging containers comprises, in the following sequence along its length:
a first end part comprising a discharge orifice;
a body part; and
a further end part; wherein the holding elements of the first kind and the holding elements of the further kind are designed and arranged such that the further end part of each primary packaging container faces the container opening or the container base when the respective primary packaging container is detachably held by one of the holding elements of the first kind.

14. The arrangement of claim 1, wherein the plurality of primary packaging containers consists of 4 to 500 primary packaging containers.

15. The arrangement of claim 1, wherein at least one of the following is satisfied:
the secondary packaging container is closed by a lid which is joined to the secondary packaging container;
the arrangement further comprises an outer packaging, wherein the secondary packaging container is arranged in the outer packaging; or
the primary packaging containers have been at least one of decontaminated or sterilized.

16. The arrangement of claim 15, further comprising a closed outer packaging, the secondary packaging container being arranged in the outer packaging.

17. The arrangement of claim 1, wherein at least one of the primary packaging containers stores a substance selected from the group consisting of a pharmaceutical composition, a medical composition, a cosmetic composition, and a combination of at least two thereof.

18. The arrangement of claim 1, wherein a holding element of the further kind is designed and arranged to restrict the movement of the primary packaging container, which is held by the holding element of the first kind, in all lateral directions of the primary packaging container.

* * * * *